(12) United States Patent
Takahashi et al.

(10) Patent No.: US 8,438,940 B2
(45) Date of Patent: May 14, 2013

(54) APPARATUS FOR SIMULATIVELY MEASURING ENVIRONMENT OF WOUND DRESSING ON SKIN AND MEASURING METHOD THEREFOR

(75) Inventors: Makoto Takahashi, Sapporo (JP); Takehiko Ohura, Sapporo (JP); Yukiko Inamoto, Takamatsu (JP); Takashi Kamakura, Kita-gun (JP); Shigeyuki Inamoto, Takamatsu (JP)

(73) Assignee: Teikoku Seiyaku Co., Ltd., Kagawa (JP)

( * ) Notice: Subject to any disclaimer, the term of this patent is extended or adjusted under 35 U.S.C. 154(b) by 317 days.

(21) Appl. No.: 12/918,367

(22) PCT Filed: Feb. 21, 2008

(86) PCT No.: PCT/JP2008/052983
§ 371 (c)(1),
(2), (4) Date: Aug. 19, 2010

(87) PCT Pub. No.: WO2009/104266
PCT Pub. Date: Aug. 27, 2009

(65) Prior Publication Data
US 2010/0326217 A1 Dec. 30, 2010

(51) Int. Cl.
*G01N 17/00* (2006.01)
(52) U.S. Cl.
USPC .............................. 73/865.6; 73/865.9; 73/38
(58) Field of Classification Search .................. 73/29.01, 73/29.02, 150 R, 159, 865.6, 866.5, 38, 865.9
See application file for complete search history.

(56) References Cited

U.S. PATENT DOCUMENTS

| 4,663,969 | A | * | 5/1987 | Bibby et al. | .................... 73/159 |
| 4,863,696 | A | * | 9/1989 | Saydek et al. | ............... 73/64.47 |
| 5,009,224 | A | | 4/1991 | Cole | |
| 5,147,698 | A | | 9/1992 | Cole | |

(Continued)

FOREIGN PATENT DOCUMENTS

| JP | 61-57834 | 3/1986 |
| JP | 63-97677 | 4/1988 |
| JP | 1-138439 | 5/1989 |
| JP | 2001-519034 | 10/2001 |

OTHER PUBLICATIONS

International Search Report issued May 13, 2008 in International (PCT) Application No. PCT/JP2008/052983.

*Primary Examiner* — Peter Macchiarolo
*Assistant Examiner* — Natalie Huls
(74) *Attorney, Agent, or Firm* — Wenderoth, Lind & Ponack, LLP

(57) ABSTRACT

An apparatus and a method for simulatively measuring an environment in a microspace between human skin and a wound dressing. The simulative environment-measuring apparatus includes a constant temperature-and-humidity chamber (14); a heat exchanger (12) disposed in the chamber; a constant temperature water bath (10) and a pump (11) for supplying warm water to the heat exchanger; and a container (1) set on the heat exchanger. The container holds a water retentive member (2) therein, and is covered with a water vapor diffusion-controlling member (4). A microspace (6) formed between the water vapor diffusion-controlling member and a wound dressing (5) is a simulatively reproduced space between human skin and the wound dressing. A thin temperature-and-humidity sensor (7) is set in the microspace to measure temperature and humidity. When plural containers are used, the environments of plural wound dressings can be measured at once.

4 Claims, 1 Drawing Sheet

U.S. PATENT DOCUMENTS

| | | | |
|---|---|---|---|
| 5,749,259 A * | 5/1998 | Hamouda et al. | 73/159 |
| 6,262,329 B1 * | 7/2001 | Brunsveld et al. | 602/54 |
| 6,298,714 B1 * | 10/2001 | Courtray | 73/73 |
| 6,308,560 B1 | 10/2001 | Bracht | |
| 6,931,951 B2 * | 8/2005 | Wright et al. | 73/866.4 |
| 7,219,534 B2 * | 5/2007 | Campbell | 73/38 |
| 7,320,261 B1 * | 1/2008 | Hockaday et al. | 73/865.9 |
| 7,458,288 B2 * | 12/2008 | Polegato Moretti | 73/865.6 |

* cited by examiner

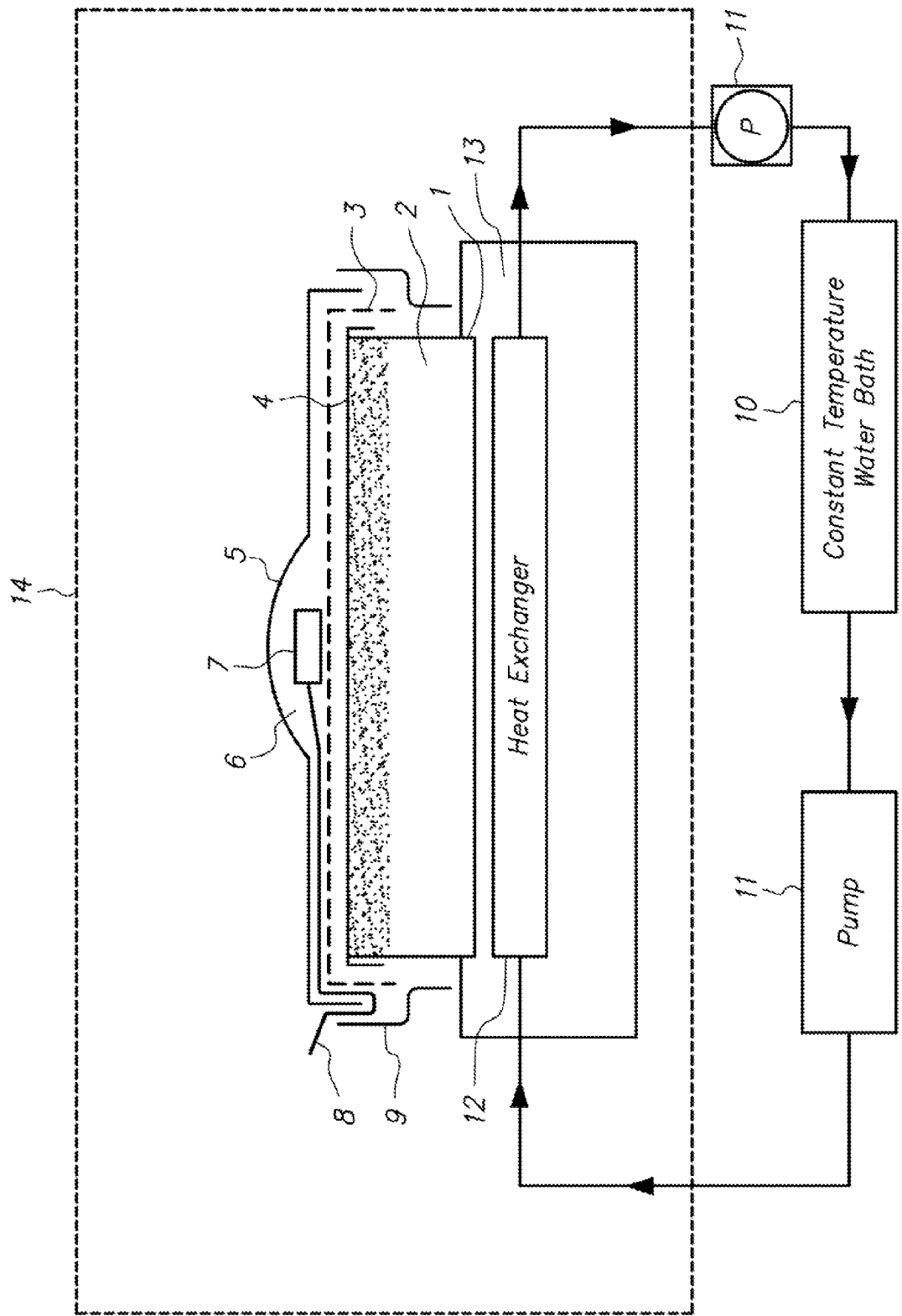

APPARATUS FOR SIMULATIVELY MEASURING ENVIRONMENT OF WOUND DRESSING ON SKIN AND MEASURING METHOD THEREFOR

BACKGROUND OF THE INVENTION

1. Technical Field

The present invention relates to an apparatus and a method for simulatively measuring an environment in a microspace between human skin and a wound dressing. In particular, the present invention pertains to an apparatus and a method for simulatively reproducing and measuring hygrothermal characteristics in a microspace between human skin and a wound dressing, at a wound area or a decubital area of the human skin being dressed for healing.

2. Description of the Related Art

The methods for healing wounds on human skin are known to be roughly classified as so-called dry dressing and so-called wet dressing. In the dry dressing, a wound area on human skin is maintained in a dried condition to form a scab on the wound area for healing. In the wet dressing, a suitably moist environment is created around a wound area to rapidly heal the wound and to lessen the dry necrosis of the surface of the wound area, and a wound-protecting effect is also produced.

In the latter method, to obtain data of a suitable moist environment, in other words, an environment in a microspace between a wound on human skin and a wound dressing, especially hygrothermal characteristics therein, is very important for healing wounds. However, measurement of hygrothermal characteristics at a wound area or a decubital area on human skin is very difficult, and measurement of such characteristics over a long period of time is much more difficult. Therefore, there hitherto has not been obtained or reported any data on an environment in a microspace between wounded skin and a wound dressing, especially hygrothermal characteristics therein.

Further, there hitherto has not been reported any simulative measuring apparatus, which is capable of reproducing conditions close to an environment in a microspace between a wound on human skin and a wound dressing, or any trial of measurement of hygrothermal characteristics in such a microspace by using such the apparatus.

Under the above-described situation, in order to study the environments for healing wounds, there arises demands for development of an apparatus and a method for simulative measurement, which make it possible to measure hygrothermal characteristics under conditions close to an environment of a microspace between wounded human skin and a wound dressing, and which make it possible to easily measure a sample without the need of a large-scaled apparatus. Further, in order to develop wound dressings, there are expected an apparatus and a method for simulative measurement, which can be readily used to evaluate wound dressings.

SUMMARY OF THE INVENTION

1. Problem to be Solved by the Invention

The object of the present invention is therefore to provide an apparatus and a method for simulatively reproducing and measuring hygrothermal characteristics in a microspace between a wound area or a decubital area on human skin and a wound dressing, while such a wound area or a decubital area is being dressed.

2. Means to Solve the Problem

An apparatus for simulatively measuring an environment, according to the present invention, comprises:
- a constant temperature-and-humidity chamber which simulatively reproduces an environment wherein a wound dressing is practically used,
- a warming unit which is disposed in the constant temperature-and-humidity chamber and warms a container holding a water content therein, up to a simulated human body temperature,
- a sample holder with water vapor permeability, which holds a sample and covers an opening of the container, and
- a sensor which measures at least one of temperature and humidity in a space between the sample holder and the sample.

Further, a method for simulatively measuring an environment, according to the present invention, comprises the following steps.
(1) Disposing a warming unit in a constant temperature-and-humidity chamber, which simulatively reproduces an environment wherein a wound dressing is practically used.
(2) Warming a container holding a water content therein, up to a simulated human body temperature, by means of the warming unit in the constant temperature-and-humidity chamber.
(3) Placing a sample of a wound dressing on a sample holder which has water vapor permeability and which is so disposed as to cover the opening of the container.
(4) Setting a sensor in a space between the sample holder and the sample to measure at least one of temperature and humidity in the space.

3. Effect of the Invention

According to the present invention, it becomes possible to simulatively reproduce an environment in a space between human skin and a wound dressing applied to the human skin and to evaluate such a local environment (temperature and humidity). Accordingly, it also becomes possible to make measurement of such an environment over a long period of time, which would be difficult if a specimen is a human body, and further, it becomes possible to definitely know hygrothermal characteristics in a space between human skin and a wound dressing. Thus, development of improved wound dressings more suitable for use can be facilitated.

Further, when plural containers are set on the warming unit within the constant temperature-and-humidity chamber, measurements of plural samples can be simply carried out at once.

BRIEF DESCRIPTION OF THE DRAWING

FIG. 1 shows a schematic diagram of an apparatus according to an embodiment of the present invention.

DESCRIPTION OF REFERENCE NUMERALS

1=container
2=water retentive member
3=sample holder
4=water vapor diffusion-controlling member
5=sample (wound dressing)
6=microspace
7=temperature and humidity sensor
8=lead wire
9=seal tape 10=constant temperature water bath
11=pump
12=heat exchanger
13=thermal insulating material
14=constant temperature-and-humidity chamber

DETAILED DESCRIPTION OF THE INVENTION

Hereinafter, a preferred embodiment of the present invention will be described with reference to the drawing. FIG. 1 shows a schematic diagram of an apparatus for simulatively measuring hygrothermal characteristics, according to an embodiment of the present invention. This apparatus is to simulatively reproduce and measure hygrothermal characteristics of a microspace between a wound dressing (or an adhesive skin patch) and human skin.

The apparatus comprises a constant temperature-and-humidity chamber 14 which controls an external environment; a heat exchanger 12 which is disposed in the chamber 14, the side walls and the bottom wall of the heat exchanger 12 being surrounded by a thermal insulating material 13; and a constant temperature water bath 10 which supplies warm water to the heat exchanger 12. The warm water is circulated through the constant temperature water bath 10 and the heat exchanger 12 by means of a pump 11. A container 1 is removably set on the heat exchanger 12.

A thermal insulating water bath is preferably used as the heat exchanger 12, of which the temperature is controllable by circulating warm water therethrough from the constant temperature water bath 10, which is disposed outside the constant temperature-and-humidity chamber 14. Temperature of the heat exchanger 12 is preferably from 30 to 40° C., more preferably within a range of 37° C.±2° C., which simulates a normal human body temperature range.

As shown in the FIGURE, the heat exchanger 12 (and the constant temperature water bath 10 and the pump 11, for circulating the warm water through the heat exchanger 12) is used as a warming unit, which warms the container 1 up to a simulated human body temperature. However, otherwise, a suitable warming unit such as an electric heater or the like may be used.

As will be described later, a sample holder 3 (optionally in combination with a water vapor diffusion-controlling member 4) is a simulated human skin, and a sample 5 (a wound dressing) is placed on the sample holder 3. A microspace 6 formed therebetween is regarded as "a microspace between human skin and a wound dressing". The temperature and humidity of this microspace 6 are measured with a sensor.

Preferably, the container 1 set on the heat exchanger 12 is made of a material which sufficiently conducts heat, for example, a metal such as stainless steel, aluminum, brass, iron, copper or the like. A water retentive member 2 is held in the container 1, and the upper opening of the container 1 is covered with the water vapor diffusion-controlling member 4, and further the sample holder 3 is set on this member 4.

The water content in the water retentive member 2 is warmed to a temperature close to a human body temperature by the heat exchanger 12 and is then vaporized to permeate the water vapor diffusion-controlling member 4 and the sample holder 3. That is, this permeation simulates sweating from human skin. Therefore, the water vapor diffusion-controlling member 4 and the sample holder 3 are needed to be made of materials, which allow permeation of water vapor.

As the water vapor diffusion-controlling member 4, there may be used a non-woven fabric, a woven fabric, cellophane, a polystyrene film (PS), any of various filter membrane, or the like. However, the water vapor diffusion-controlling member 4 can be omitted, depending on simulated conditions for a wound area or a decubital area covered with a wound dressing. With various combinations of the water retentive member 2 and the water vapor diffusion-controlling member 4, there can be variously set the simulated conditions for an environment around the wound area or the decubital area covered with the wound dressing.

That is: in a case where human skin is in a wet condition because of much exudate from a wound area or a decubital area, a water retentive member 2 made of a material sufficient in hydrous property and transpiration property is selected. Sufficient water is absorbed in this water retentive member 2, and then the water retentive member 2 is set in the container 1, where hygrothermal characteristics are measured without a water vapor diffusion-controlling member 4.

On the other hand, in a case where little exudate oozes from a wound area or a decubital area on a skin, a water retentive member 2 made of a material inferior in hydrous property and transpiration property is selected, and water is absorbed therein. Measurement of hygrothermal characteristics is conducted, with using a material capable of inhibiting diffusion of water vapor to a certain degree, as the water vapor diffusion-controlling member 4. Further, also for a case of human skin in a normal condition, it is possible to set simulated conditions.

The sample holder 3 is intended to hold the sample 5 thereon, and to cover the opening of the container 1. Therefore, a material for the sample holder 3 preferably has a suitable strength, and permits easy removal of the sample after the completion of a test. For example, a thin plate of Teflon®, a thin plate coated with silicone, a thin plate coated with a fluororesin, or the like is used, among which a thin plate of Teflon® is preferable.

The sample holder 3 is also required to have water vapor permeability, and is therefore made having a mesh texture or having appropriate openings therein.

As a material for the water retentive member 2, there may be used materials having water-retaining properties, i.e., cellulose, polyvinyl alcohol (PVA), urethane, melamine resins, sponge or the like, etc. The water contents and transpiration amounts depend on the materials. Therefore, a material suitable for target measuring conditions may be selected. The water retentive member 2 is immersed in water to hold a sufficient amount of water therein before the start of a test, and is then set in the container 1.

In this connection, it is sufficient only if the container 1 holds water content therein, and therefore, water may be directly put into the container, without using the water retentive member 2.

As the sample 5, there may be used any of a variety of wound dressings, poultices, tapes or plasters.

A temperature-and-humidity sensor is used to measure the temperature and humidity in the microspace 6 formed between the sample holder 3 and the sample 5. While a temperature sensor and a humidity sensor may be used separately, a temperature-and-humidity sensor capable of measuring both of them is preferably used. For convenience of measurement, a temperature-and-humidity sensor of small size and thickness is preferably used.

The constant temperature-and-humidity chamber 14 for controlling an external environment is preferably one, which is controllable within ranges of 20 to 40° C. in temperature and 25 to 99% RH in humidity, and is also changeable in air flow amount. This is for simulating an environment wherein a wound dressing is practically used, that is, for reproducing a normal indoor environment or an environment inside a quilt (or bedclothes).

The preferable conditions of the external environment are 20 to 40° C. in temperature and 30 to 80% RH in humidity, more preferably, 25 to 35° C. in temperature and 40 to 60% RH in humidity.

A method for measurement according to the present invention will be described below.

The heat exchanger 12 is set within the constant temperature-and-humidity chamber 14, and then, warm water from the constant temperature bath 10 disposed outside the chamber 14 is circulated by means of the pump 11, to thereby preliminarily warm the heat exchanger 12 up to a temperature equivalent to a local body temperature. Simultaneously, the container 1 set on the heat exchanger 12 is also preliminarily warmed (at this time, the sample 5 is not placed on the sample holder 3).

After the preliminarily warming, the weight of "the sample 5" and the weight of "the container 1 without the sample 5" are measured, respectively (the measuring step 1). A thin temperature-and-humidity sensor 7 is set on the sample holder 3 on the container 1, and the sample 5 is placed on the sensor 7. After that, the container 1 is sealed at its periphery with a seal tape 9 so that water vapor does not leak out, and the container 1 is again set on the heat exchanger 12.

The temperature-and-humidity sensor 7 is set in the microspace 6 between the sample holder 3 and the sample 5, and is connected to a measuring device (not shown) disposed outside the constant temperature-and-humidity chamber 14, through a lead wire 8, so as to output measured values of temperature and humidity with time.

Plural samples 5 would be measured at once, if plural containers 1 are set on the heat exchanger 12.

While temperature and humidity within the microspace 6 are being measured with the temperature-and-humidity sensor 7 with time, the total weight of the container 1 (including the sample 5 set thereon) is also measured with time, on the other hand (the measuring step 2). This measurement may be done, for example, with a weighing unit (not shown) which is disposed in the constant temperature-and-humidity chamber 14.

Subtracting the total weight of the container 1 obtained in "the measuring step 2", from the total weight of "the sample 5" and "the container 1 without sample 5" obtained in "the measuring step 1", then the amount of the transpired water content in the container 1 also can be measured with time (the measuring step 3).

After the completion of the test, the weight of the sample 5 alone is measured. From this weight of the sample alone, the weight of the sample 5 obtained in "the measuring step 1" is subtracted. By this calculation, the water absorption amount of the sample 5 itself can be obtained. This water absorption amount is subtracted from the final amount of the transpired water content obtained in "the measuring step 3" to determine the amount of the water vapor which has permeated the sample 5. Further, this amount of the water vapor permeated is divided by the test time to obtain "humidity permeability of the sample 5 per hour".

Next, the present invention will be described in more detail by way of Examples, which however should not be construed as limiting the scope of the present invention in any way. In each of Examples, the following commercially available products "A" to "D" of wound dressings for healing decubitus were used as the samples 5.

Product "A" (component: hydrocolloid)
Product "B" (component: polyurethane film)
Product "C" (component: hydrogel)
Product "D" (component: polyurethane film)

Example 1

The commercially available products "A" and "B" (wound dressings) were used as the samples 5, and humidity, one of the factors of an external environment, was investigated.

The container 1 having the water retentive member 2 and the water vapor diffusion-controlling member 4 previously set therein was placed on the heat exchanger 12, which was set in the constant temperature-and-humidity chamber 14 for controlling an external environment (EYELA constant temperature-and-humidity chamber KCL-2000W manufactured by TOKYO RIKAKIKAI CO., LTD.), and the container 1 was preliminarily warmed.

After the preliminary warming, the sample 5 (the commercially available wound dressings) and the temperature-and-humidity sensor 7 (digital temperature-and-humidity sensors TRH-CA, manufactured by SHINYEI KAISHA) were set to the container 1. For the external environment, simulating an inner condition of bedclothes, temperature was set at 35° C. and humidity was set at 40% RH, 50% RH and 60% RH. In these conditions, humidity and temperature in the microspaces 6 were examined with time. The results of the measurement are shown in Tables 1 and 2.

When 60 minutes had passed from the start of the measurement, in the conditions where the exudates were found in the decubital areas (wet condition), there was almost no variation on the temperature and the humidity in the microspace 6, in both of the commercially available products "A" and "B". On the other hand, in the conditions where no exudates were found in the decubital areas (dried condition), there was almost no variation on the temperature in the microspace 6, but the humidity in the microspace 6 increased with the increase of the humidity of the external environment.

TABLE 1

| | | | | | | | |
|---|---|---|---|---|---|---|---|
| (Product A) | | | | | | | |
| External humidity | Condition of decubital | Water retentive | Water vapor diffusion-controlling | Humidity (% RH)/Temperature (° C.) in microspace | | | |
| (% RH) | area★ | member | member | 15 min. later | 30 min. later | 45 min. later | 60 min. later |
| 40 | presence | PVA | — | 96.8/32.8 | 97.0/33.0 | 96.5/33.1 | 96.7/33.1 |
| | presence | Cellulose | — | 98.9/32.2 | 99.0/33.1 | 98.5/33.4 | 98.8/33.7 |
| | absence | Urethane | — | 36.5/34.4 | 36.7/34.8 | 38.1/34.8 | 39.9/34.9 |
| 50 | presence | Cellulose | — | 99.7/32.9 | 99.6/33.7 | 99.6/33.9 | 99.8/34.1 |
| | absence | Urethane | — | 36.7/34.6 | 37.4/35.1 | 38.9/35.0 | 40.1/35.1 |
| 60 | presence | PVA | — | 97.9/33.8 | 98.0/34.0 | 98.1/34.1 | 98.0/34.2 |
| | absence | Urethane | — | 45.5/34.9 | 47.2/35.2 | 49.5/35.2 | 50.8/35.2 |

★presence or absence of exudate

TABLE 2

(Product B)

| External humidity (% RH) | Condition of decubital area★ | Water retentive member | Water vapor diffusion-controlling member | Humidity (% RH)/Temperature (° C.) in microspace | | | |
|---|---|---|---|---|---|---|---|
| | | | | 15 min. later | 30 min. later | 45 min. later | 60 min. later |
| 40 | presence | PVA | — | 99.5/33.7 | 99.2/34.6 | 99.5/35.0 | 99.7/35.2 |
| | presence | Cellulose | — | 92.3/31.5 | 92.8/32.7 | 93.1/33.3 | 93.8/33.4 |
| | absence | Urethane | — | 41.6/34.8 | 42.1/34.9 | 42.2/35.0 | 42.7/34.9 |
| 50 | presence | Cellulose | — | 98.2/33.4 | 98.9/33.9 | 99.5/34.1 | 99.7/34.3 |
| | absence | Urethane | — | 42.2/34.8 | 44.6/35.0 | 47.4/35.0 | 48.8/35.0 |
| 60 | presence | PVA | — | 90.3/33.2 | 90.6/33.5 | 91.9/33.5 | 93.6/34.2 |
| | absence | Urethane | — | 47.2/35.3 | 51.2/35.3 | 55.8/35.2 | 57.4/35.2 |

★presence or absence of exudate

Example 2

A variety of water retentive members 2 and water vapor diffusion-controlling members 4 were examined, with the use of the commercially available products "A" and "B" (the wound dressings) as the samples 5, like in Example 1. The external environment was set at 35° C. in temperature and at 40% RH in humidity. The results are shown in Table 3.

It was found that with various combinations of the water retentive members 2 and the water vapor diffusion-controlling members 4, it is possible to control the humidity in the microspaces 6, and to simulatively reproduce the presence or absence of the exudates on the decubital areas.

TABLE 3

| Product | Condition of decubital area★ | Water retentive member | Water vapor diffusion-controlling member | Humidity (% RH)/Temperature (° C.) in microspace | | | |
|---|---|---|---|---|---|---|---|
| | | | | 15 min. later | 30 min. later | 45 min. later | 60 min. later |
| A | presence | PVA | — | 96.8/32.8 | 97.0/33.0 | 96.5/33.1 | 96.7/33.1 |
| | presence | Cellulose | — | 98.9/32.2 | 99.0/33.1 | 98.5/33.4 | 98.8/33.7 |
| | somewhat | PVA | Cellophane | 96.0/33.4 | 97.0/34.1 | 97.6/34.4 | 98.4/34.6 |
| | somewhat | Cellulose | Cellophane | 98.2/34.5 | 98.1/34.5 | 98.4/34.5 | 98.4/34.8 |
| | almost none | Cellulose | PS | 71.7/33.3 | 74.1/34.2 | 75.7/34.7 | 76.9/34.9 |
| | absence | Urethane | — | 36.5/34.4 | 36.7/34.8 | 38.1/34.8 | 39.9/34.9 |
| B | presence | PVA | — | 99.5/33.7 | 99.2/34.6 | 99.5/35.0 | 99.7/35.2 |
| | presence | Cellulose | — | 92.3/31.5 | 92.8/32.7 | 93.1/33.3 | 93.8/33.4 |
| | somewhat | PVA | Cellophane | 92.0/32.4 | 94.4/32.6 | 95.7/33.1 | 96.6/33.5 |
| | somewhat | Cellulose | Cellophane | 95.6/32.7 | 95.8/33.5 | 96.4/34.0 | 96.9/34.4 |
| | almost none | Cellulose | PS | 62.2/32.3 | 59.3/33.2 | 58.7/33.9 | 58.6/34.3 |
| | absence | Urethane | — | 41.6/34.8 | 42.1/34.9 | 42.2/35.0 | 42.7/34.9 |

*External environment: 35° C., 40% RH
★presence or absence of exudate

Example 3

Changes of humidity and temperature in the microspaces 6 during a short time period were measured with time, with the use of the commercially available products "A", "B", "C" and "D" (the wound dressings) as the samples 5, like in Example 1. The external environment was set at 35° C. in temperature and at 40% RH in humidity. The results are shown in Table 4.

In the conditions where the exudates were present in the decubital areas, there was almost no variation on the temperature and the humidity in the microspaces 6, in the four commercially available products. But, in the conditions where almost no exudates were in the decubital areas, the humidity in the microspaces 6 for the commercially available products "B" and "D" were found to be slightly lower than that for the commercially available product "A". This was supposed to come from the difference of the compositions of the products.

TABLE 4

| Product | Condition of decubital area★ | Water retentive member | Water vapor diffusion-controlling member | Humidity (% RH)/Temperature (° C.) in microspace | | | |
|---|---|---|---|---|---|---|---|
| | | | | 15 min. later | 30 min. later | 45 min. later | 60 min. later |
| A | presence | Cellulose | — | 96.2/34.4 | 98.9/33.9 | 98.1/34.2 | 98.0/34.3 |
| | almost none | Cellulose | PS | 71.7/33.3 | 74.1/34.2 | 75.7/34.7 | 76.9/34.9 |

TABLE 4-continued

| Product | Condition of decubital area★ | Water retentive member | Water vapor diffusion-controlling member | Humidity (% RH)/Temperature (° C.) in microspace | | | |
|---|---|---|---|---|---|---|---|
| | | | | 15 min. later | 30 min. later | 45 min. later | 60 min. later |
| B | presence | Cellulose | — | 90.9/32.2 | 92.1/32.7 | 92.8/33.2 | 93.6/33.5 |
|   | almost none | Cellulose | PS | 62.2/32.3 | 59.2/33.2 | 58.7/33.9 | 58.6/34.3 |
| C | presence | Cellulose | — | 99.4/33.3 | 99.4/33.7 | 99.1/33.4 | 98.6/33.6 |
|   | almost none | Cellulose | PS | — | — | — | — |
| D | presence | Cellulose | — | 95.5/32.3 | 96.9/33.1 | 97.5/33.4 | 97.8/33.6 |
|   | almost none | Cellulose | PS | 64.1/32.5 | 62.2/33.6 | 61.1/34.3 | 60.9/34.5 |

*External environment: 35° C., 40% RH
★presence or absence of exudate

Example 4

Changes of the humidity and the temperature in the microspaces 6 during a long time period were measured with time, with the use of the commercially available products "A", "B", "C" and "D" (the wound dressings) as the samples 5, like in Example 1. The external environment was set at 35° C. in temperature and at 40% RH in humidity. The results are shown in Table 5.

In each condition of the decubital areas, the humidity in the microspaces 6 was kept within a range of 95 to 99% RH for 24 hours after the start of the measurement, in all the products, and the temperature therein was kept constant around 35° C.

TABLE 5

| Product | Condition of decubital area★ | Water retentive member | Water vapor diffusion-controlling member | Humidity (% RH)/Temperature (° C.) in microspace | | | | |
|---|---|---|---|---|---|---|---|---|
| | | | | 1 hour later | 2 hour later | 4 hour later | 8 hour later | 24 hour later |
| A | presence | Cellulose | — | 99.1/34.2 | 98.6/34.4 | 98.8/34.4 | 97.6/34.4 | 97.9/34.4 |
|   | somewhat | Cellulose | Cellophane | 98.3/35.0 | 98.4/35.1 | 98.4/35.1 | 98.4/34.8 | 98.4/35.2 |
| B | presence | Cellulose | — | 96.9/34.4 | 97.8/34.7 | 97.8/34.7 | 98.4/34.8 | 98.2/34.7 |
|   | somewhat | Cellulose | Cellophane | 89.9/33.7 | 94.3/34.0 | 93.9/34.1 | 94.1/34.3 | 93.2/34.4 |
| C | presence | Cellulose | — | 98.4/34.3 | 99.3/34.5 | 97.3/34.4 | — | 96.0/34.4 |
| D | presence | Cellulose | — | 96.0/34.2 | — | 96.7/34.3 | 95.9/34.3 | 95.2/34.4 |

*External environment: 35° C., 40% RH
★presence or absence of exudate

As can be understood from the results of the above-described Examples, by using the simulative environment-measuring apparatus of the present invention, which is capable of simulatively reproducing and measuring an environment of a microspace between human skin and a wound dressing, it becomes possible to obtain the data of a suitable wet environment as one of important factors for healing of wounds, in other words, the data of an environment of a microspace between a wound on human skin and a wound dressing, especially the data of hygrothermal characteristics of such a microspace over a long period of time.

The simulative environment-measuring apparatus of the present invention is very useful not only for the evaluation of the existing wound dressings but also for development of novel wound dressings.

The invention claimed is:

1. An apparatus for simulatively measuring an environment in a microspace between a wound on human skin and a wound dressing, the apparatus comprising:
    a constant temperature-and-humidity chamber which simulatively reproduces an environment in which a wound dressing is practically used,
    a warming unit which is disposed in the constant temperature-and-humidity chamber and warms a container holding therein a water retentive member, which holds water, up to a simulated human body temperature,
    a water vapor diffusion-controlling member, which covers an opening of the container and controls the permeation of water vapor,
    a sample holder with water vapor permeability, the sample holder being provided on the water vapor diffusion-controlling member to hold a sample thereon such that a closed space simulating the microspace is formed between the sample holder and the sample, and
    a sensor which measures temperature and/or humidity in the closed space between the sample holder and the sample.

2. The apparatus of claim 1, wherein a plurality of the containers are provided.

3. The apparatus of claim 1, wherein the sensor is a temperature-and-humidity sensor capable of measuring temperature and humidity.

4. A method for simulatively measuring an environment in a microspace between a wound on human skin and a wound dressing, the method comprising the steps of:
    disposing a warming unit in a constant temperature-and-humidity chamber, which simulatively reproduces an environment wherein a wound dressing is practically used,
    warming a container holding a water content therein, up to a simulated human body temperature, by means of the warming unit in the constant temperature-and-humidity chamber,
    placing a sample of a wound dressing on a sample holder, which has water vapor permeability and which is provided on a water vapor diffusion-controlling member, which covers an opening of the container and controls permeation of water vapor, such that a closed space simulating the microspace is formed between the sample holder and the sample, and setting a sensor in the closed space between the sample holder and the sample to measure temperature and/or humidity in the space.

\* \* \* \* \*